United States Patent [19]

Chenard

[11] Patent Number: 4,795,817
[45] Date of Patent: Jan. 3, 1989

[54] 8-SUBSTITUTED PYRAZOLOPENTATHIEPINS AND RELATED COMPOUNDS

[75] Inventor: Bertrand L. Chenard, Wilmington, Del.

[73] Assignee: E. I. Du Pont de Nemours and Company, Wilmington, Del.

[21] Appl. No.: 831,542

[22] Filed: Feb. 21, 1986

Related U.S. Application Data

[63] Continuation-in-part of Ser. No. 543,195, Oct. 18, 1983, abandoned.

[51] Int. Cl.$^4$ ............................................. C07D 495/04
[52] U.S. Cl. ...................................... 548/370; 549/11; 548/126
[58] Field of Search ......................................... 548/370

[56] References Cited

U.S. PATENT DOCUMENTS 4,094,985  6/1978  Vladuchick ........................ 424/270
4,275,073  6/1981  Moberg ............................ 424/273 P

FOREIGN PATENT DOCUMENTS 0056475 12/1981 European Pat. Off. .

OTHER PUBLICATIONS

Gotthardt et al., Chem. Ber. 112, 1206 (1979).
Bull. Soc. Chim. Belg., 86, 679 (1977).
J. Het. Chem., 13, 301 (1976) and 15, 473 (1978).
Khim. Geterotsikl. Soedin. 4, 477 (1979).
Bull. Chem. Soc. Jap., 44, 2856 (1971).
J. Het. Chem., 19, 1267 (1982).

Primary Examiner—Robert Gerstl
Attorney, Agent, or Firm—James A. Costello

[57] ABSTRACT

Heteropentathiepins including pyrazolopentathiepins substituted in the 8-position; intermediate pyrazolo-1,2,3-thiadiazoles, pyrazolothiazathiolium chlorides, and 5-substituted aminopyrazoles; process for making the pentathiepins by reacting the corresponding 1,2,3-thiadiazoles with sulfur at elevated temperatures; process for making the thiazathiolium chlorides; and use of the pentathiepins as fungicides or as sulfur sensitizers in photographic emulsions.

6 Claims, No Drawings

8-SUBSTITUTED PYRAZOLOPENTATHIEPINS AND RELATED COMPOUNDS

CROSS-REFERENCE TO RELATED APPLICATION

This is a continuation-in-part of copending application bearing Ser. No. 543,195 filed on Oct. 18, 1983, abandoned.

BACKGROUND OF THE INVENTION

This invention concerns hetero fused pentathiepins, 1,2,3-thiadiazoles, thiazathiolium chlorides, aminopyrazoles, and a method for making thiazathiolium chlorides and pentathiepins.

Although certain pyrazolopentathiepins are known, none appear to have been disclosed which are substituted in the 8-position. Representative of the state of the art relative to the hetero fused pentathiepins of this invention are the following publications.

U.S. Pat. No. 4,275,073 discloses 7-substituted pyrazolopentathiepins and their use as fungicides:

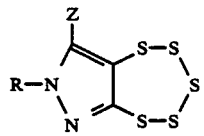

where R=H, or other substituent. However, the patent is limited to the pyrazolopentathiepins where Z is H and the synthetic methods disclosed cannot be used to prepare the compounds of this invention.

U.S. Pat. No. 4,094,985 discloses these isothiazolopentathiepins as fungicides:

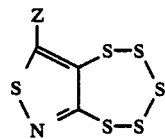

and is limited to compounds where Z is CH, COOCl, $COOR^1$, $COSR^1$ or $CONR^2R^3$ and $R^1$ is hydrogen or alkyl of 1-2 carbon atoms, $R^2$ is hydrogen or methyl and $R^3$ is hydrogen, alkyl of 1-4 carbon atoms or phenyl. The synthetic methods disclosed in this patent cannot be used to prepare the structures of this invention where Z is a substitutent other than those listed above.

Perregaard et al., Bull. Soc. Chim. Belg., 86, 679 (1977) discloses:

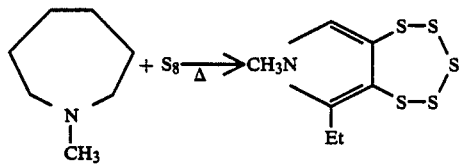

Pyrazolo-1,2,3-thiadiazoles appear to be unknown. Representative of the state of the art relative to the thiadiazoles of this invention is: Shafiee, J. Het. Chem., 13, 301 (1976) and 15, 473 (1978) which discloses:

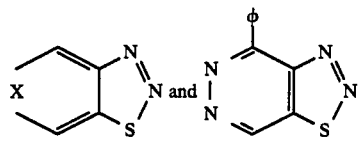

X=S, Se, NR.

Representative of the state of the art relative to the thiazathiolium chlorides of this invention are: Abramenko et al., Khim. Geterotsikl. Soedin. 4, 477 (1979) which discloses:

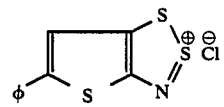

EPO application No. 0,056,475 discloses the preparation of thiazathiolium chlorides but does not disclose the preparation of pyrazolothiazathiolium chlorides.

Representative of the state of the art relative to aminopyrazoles are: Hori and Igarashi, Bull. Chem. Soc. Jap., 44, 2856 (1971) which disclose:

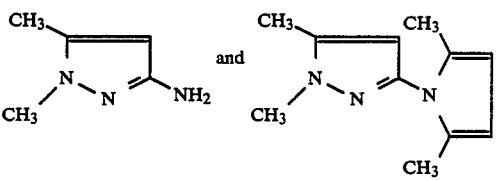

and Ege et al., J. Het. Chem., 19, 1267 (1982) which disclose other substituted aminopyrazoles.

SUMMARY OF THE INVENTION

This invention concerns a process for making pentathiepins by the following reactions:

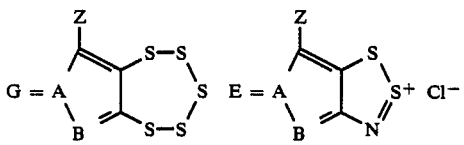

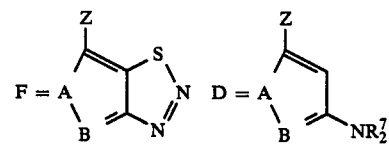

wherein:

A is $R^1N$, S or $CR^2$;
B is N, $CR^2$ or S;
Z is H, halogen, CN, $R^3$, $OR^4$, $SR^4$, $NR^5R^4$, $COOR^4$, $COSR^4$, or $CONR^5R^4$;
$R^1$, $R^2$, $R^3$, $R^4$, and $R^5$ are the same or different and are selected from the group H, except that $R^1$ is not H, $C_1$ to $C_6$ straight or branched alkyl, $C_3$ to $C_6$ cycloalkyl, phenyl, naphthyl and substituted phenyl and naphthyl with 1 to 5 hydrogen atoms of phenyl and 1 to 7 hydrogen atoms of naphthyl substituted with substituents selected from the group $R^6$, halogen, $OR^6$, $NR_2^6$ with $R^6=C_1$ to $C_6$ straight or branched alkyl;

$R^2$ additionally can include CN, $NO_2$, $COOR^4$, $OR^4$, $SR^4$, $NR^4R^5$, $COSR^4$, and $CONR^5R^4$; and $R^7$ is H.

A reducing agent is employed in preparation of F from E. Representative of such reducing agents are $Na_2S_2O_4$ and $NaHSO_3$. Also employed is a compound $MNO_2$ or $RONO$ wherein M is selected from $Li^+$, $Na^+$, $K^+$ and $NH_4^+$ and R is $C_1$ to $C_{10}$ straight or branched alkyl.

Appropriate care should be taken to protect Z from reaction with sulfur when $R^4$ and/or $R^5$ is H. Suitable protecting groups are described in McOmie, "Protective Groups in Organic Chemistry", Plenum Press, New York (1973).

This invention also concerns novel hetero-ring fused pentathiepins of the formula:

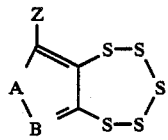

wherein:

I

A is $R^1N$,

B is N,

Z is halogen, CN, $OR^4$, $SR^4$, $NR^5R^4$, $COOR^4$, $COSR^4$, or $CONR^5R^4$, and $R^1$, $R^4$, and $R^5$ are the same or different and are selected from the group H, except that $R^1$ is not H, $C_1$ to $C_6$ straight or branched alkyl, $C_3$ to $C_6$ cycloalkyl, phenyl, naphthyl and substituted phenyl and naphthyl with 1 to 5 hydrogen atoms of phenyl and 1 to 7 hydrogen atoms of naphthyl substituted with substituents selected from the group $R^6$, halogen, $OR^6$, $NR_2^6$ with $R^6=C_1$ to $C_6$ straight or branched alkyl;

II

A is S,

B is $CR^2$; and

III

A is $CR^2$, B is S, wherein for II and III:

Z is H, halogen, CN, $OR^4$, $SR^4$, $NR^5R^4$, $COOR^4$, $COSR^4$, or $CONR^5R^4$;

$R^2$, $R^4$, and $R^5$ are the same or different and are selected from the group H, $C_1$ to $C_6$ straight or branched alkyl, $C_3$ to $C_6$ cycloalkyl, phenyl, naphthyl and substituted phenyl and naphthyl with 1 to 5 hydrogen atoms of phenyl and 1 to 7 hydrogen atoms or naphthyl substituted with substituents selected from the group $R^6$, halogen, $OR^6$, $NR_2^6$ with $R^6=C_1$ to $C_6$ straight or branched alkyl; and $R^2$ additionally can include CN, $NO_2$, $COOR^4$, $OR^4$, $SR^4$, $NR^4R^5$, $COSR^4$, and $CONR^5R^4$.

Preferred penthathiepins are those wherein:

IV

A is $R^1N$, B is N, Z is halogen, CN, $COOR^4$;

V

A is S, B is $CR^2$, Z is halogen, CN, $COOR^4$;

wherein for IV and V:

$R^1$, $R^2$, $R^4$ and $R^5$ are the same or different and are selected from the group H, except that $R^1$ is not H, $C_1$ to $C_6$ straight or branched alkyl, $C_3$ to $C_6$ cycloalkyl, phenyl, naphthyl and substituted phenyl and naphthyl with 1 to 5 hydrogen atoms of phenyl and 1 to 7 hydrogen atoms of naphthyl substituted with substituents selected from the group $R^6$, halogen, $OR^6$, $NR_2^6$ with $R^6=C_1$ to $C_6$ straight or branched alkyl; and $R^2$ additionally can include CN, $NO_2$, $COOR^4$, $OR^4$, $SR^4$, $NR^4R^5$, $COSR^4$ and $CONR^5R^4$.

Most preferred penthathiepins are those of IV wherein:

VI

Z is halogen or CN, and $R^1$ and $R^4$ are the same or different and are selected from the group $C_1$ to $C_6$ straight or branched alkyl, $C_3$ to $C_6$ cycloalkyl, phenyl, naphthyl and substituted phenyl and naphthyl with 1 to 5 hydrogen atoms of phenyl and 1 to 7 hydrogen atoms of naphthyl substituted with substituents selected from the group $R^6$, halogen, $OR^6$, $NR_2^6$ with $R^6=C_1$ to $C_6$ straight or branched alkyl.

This invention also concerns hetero-ring-fused 1,2,3-thiadiazoles of the formula:

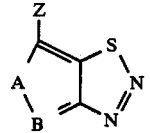

wherein:

A is $R^1N$,

B is N,

Z is H, halogen, CN, $OR^4$, $SR^4$, $NR^5R^4$, $COOR^4$, $COSR^4$, or $CONR^5R^4$, $R^1$, $R^4$, and $R^5$ are the same or different and are selected from the group H, except that $R^1$ is not H, $C_1$ to $C_6$ straight or branched alkyl, $C_3$ to $C_6$ cycloalkyl, phenyl, naphthyl and substituted phenyl and naphthyl with 1 to 5 hydrogen atoms of phenyl and 1 to 7 hydrogen atoms of naphthyl substituted with substituents selected from the group $R^6$, halogen, $OR^6$, $NR_2^6$ with $R^6=C_1$ to $C_6$ straight or branched alkyl.

Preferred 1,2,3-thiadiazoles are those wherein:

Z is halogen, CN, $COOR^4$, and $R^1$ and $R^4$ are the same or different and are selected from the group H, except that $R^1$ is not H, $C_1$ to $C_6$ straight or branched alkyl, $C_3$ to $C_6$ cycloalkyl, phenyl, naphthyl and substituted phenyl and naphthyl with 1 to 5 hydrogen atoms of phenyl and 1 to 7 hydrogen atoms of naphthyl substituted with substituents selected from the group $R^6$, halogen, $OR^6$, $NR_2^6$ with $R^6=C_1$ to $C_6$ straight or branched alkyl.

Most preferred 1,2,3-thiadiazoles are those wherein:

Z is halogen or $COOR^4$, and $R^1$ and $R^4$ are the same or different and are selected from the group $C_1$ to $C_6$ straight or branched alkyl, $C_3$ to $C_6$ cycloalkyl, phenyl, naphthyl and substituted phenyl and naphthyl with 1 to 5 hydrogen atoms of phenyl and 1 to 7 hydrogen atoms of naphthyl substituted with substituents selected from the group R⁶, halogen, OR⁶, NR₂⁶ with R⁶=C₁ to C₆ straight or branched alkyl.

This invention also concerns novel pyrazolothiazathiolium chlorides of the formula

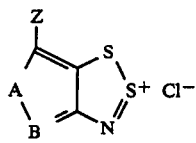

wherein:
A is R¹N,
B is N,
Z is H, halogen, CN, OR⁴, SR⁴, NR⁵R⁴, COOR⁴, COSR⁴, or CONR⁵R⁴,
R¹, R⁴, and R⁵ are the same or different and are selected from the group H, except that R¹ is not H, C₁ to C₆ straight or branched alkyl, C₃ to C₆ cycloalkyl, phenyl, naphthyl and substituted phenyl and napthyl with 1 to 5 hydrogen atoms of phenyl and 1 to 7 hydrogen atoms of naphthyl substituted with substituents selected from the group R⁶, halogen, OR⁶, NR₂⁶ with R⁶=C₁ to C₆ straight or branched alkyl.

Preferred pyrazolothiazathiolium chlorides are those wherein:
Z is halogen, CN, COOR⁴,
R¹ and R⁴ are the same or different and are selected from the group H, except that R¹ is not H, C₁ to C₆ straight or branched alkyl, C₃ to C₆ cycloalkyl, phenyl, naphthyl and substituted phenyl and naphthyl with 1 to 5 hydrogen atoms of phenyl and 1 to 7 hydrogen atoms of naphthyl substituted with substituents selected from the group R⁶, halogen, OR⁶, NR₂⁶ with R⁶=C₁ to C₆ straight or branched alkyl.

Most preferred pyrazolothiazathiolium chlorides are those wherein:
Z is halogen or COOR⁴; and
R¹ and R⁴ are the same or different and are selected from the group C₁ to C₆ straight or branched alkyl, C₃ to C₆ cycloalkyl, phenyl, naphthyl and substituted phenyl and naphthyl with 1 to 5 hydrogen atoms of phenyl and 1 to 7 hydrogen atoms of naphthyl substituted with substituents selected from the group R⁶, halogen, OR⁶, NR₂⁶ with R⁶=C₁ to C₆ straight or branched alkyl.

This invention also concerns a process for making pyrazolothiazathiolium chlorides, E, by reacting D with S₂Cl₂.

This invention also concerns novel aminopyrazoles of the formula

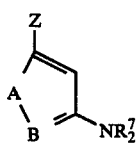

wherein:
A is R¹N,
B is N,
Z is halogen, CN, OR⁴, SR⁴, NR⁵R⁴, COOR⁴, COSR⁴, or CONR⁵R⁴,
R¹, R⁴, and R⁵ are the same or different and are selected from the group H, except tthat R¹ is not H, C₁ to C₆ straight or branched alkyl, C₃ to C₆ cycloalkyl, phenyl, naphthyl and substituted phenyl and naphthyl with 1 to 5 hydrogen atoms of phenyl and 1 to 7 hydrogen atoms of naphthyl substituted with substituents selected from the group R⁶, halogen, OR⁶, NR₂⁶ with R⁶=C₁ to C₆ straight or branched alkyl; and
R⁷ is H or

DETAILS OF THE INVENTION

Compounds D are prepared by the reaction of 1-substituted-3-aminopyrazoles with acetonylacetone and acid catalyst followed by reaction with a base such as n-butyllithium, t-butyllithium, phenyllithium or lithium diisopropylamide at about −80° C. to −50° C. in nonprotic solvents (THF or ether) and subsequent reaction with an electrophile such as cyanogen halides, alkyl halides, alkyl or aryl chloroformates. The reaction with acetonylacetone is simply to protect the amino group during subsequent functionalization at position 5.

Removal of the protecting group is accomplished by reaction of the compound with hydroxylamine hydrochloride and alcoholic alkali solution such as KOH or NaOH in methanol or ethanol, or aqueous combinations of these solvents. The reaction occurs at 50° to 120° C.; 60° to 90° C. gives best results.

Preparation of compounds E from compounds D is accomplished by reacting compounds D with S₂Cl₂. This reaction, known as the Hetero-Herz reaction, requires an inert atmosphere (nitrogen, helium, argon) and proceeds at −20° to 80° C. Excess S₂Cl₂ with acid diluent, such as acetic acid, works well as does neat S₂Cl₂ and an acid salt of D.

The conversion of compounds E to compounds F is by base hydrolysis and reduction followed by diazotization. Suitable bases include alkali-metal hydroxides or bicarbonates; suitable reducing agents are bisulfites and hydrosulfite.

The method for making compounds G is by reacting the corresponding 1,2,3-thiadiazoles with elemental sulfur at elevated temperatures. The reaction temperature is maintained at about 80° to 200° C.; the preferred range is about 110° C. to 170° C. It is carried out in inert solvents which do not react with sulfur and which boil at or above the reaction temperatures. Acceptable solvents include but are not limited to pyridine, decahydronaphthalene, dimethyl sulfoxide, xylenes, dichlorobenzenes.

The process can be carried out at atmospheric pressure or at elevated pressures which allow the use of lower-boiling solvents at elevated temperatures. There is no requirement for an inert atmosphere, although one can be used. The molar ratio of sulfur (calculated as S₈) to thiadiazole can be from about 1:2 to 2:1; the preferred ratio is about 1:1.

A relatively non-volatile, tertiary organic amine can be added to lower the reaction temperature. Examples of such amines include pyridine and 1,4-diazabicyclo[2.2.2]octane; the latter being preferred.

Utility

The pentathiapins of this invention are useful as fungicides. The following Table summarizes the activity of selected pentathiepins as fungicides. The 8-bromo-7-methylpyrazolopentathiepin was 100% effective against apple scab at only 16 ppm (in addition to 100% effectiveness at the concentration noted).

TABLE 1

| Compound (at 100 ppm) | Preventive Disease Control, Percent | | | |
|---|---|---|---|---|
| | Apple Scab | Wheat Rust | Bean Botrytis | Peanut Cercospora |
| 8-Bromo-7-methyl-pyrazolopentathiepin | 100 | 80 | 77 | Not Tested |
| 8-Cyano-7-methyl-pyrazolopentathiepin | 100 | 90 | 70 | 90 |
| 6-Phenylthieno-pentathiepin | 50 | 0 | 0 | 0 |

Control formulations were prepared by dissolving 15 mg of the pentathiepin in 5 mL of acetone, diluting the solution to 150 mL with distilled water and adding TREM 014 surfactant (polyhydric alcohol esters). The solutions were sprayed onto the appropriate host plant to the point of run-off and the host plants innoculated with fungal pathogen and incubated. Percent disease control was made by comparison of experimental and control plants.

The percent control in Table 1 was calculated according to the following formula:

% Control = 100 − [A/B × 100]

where A = disease rating on treated plants and B = disease rating on untreated plants.

PLANT FUNGAL CONTROL FORMULATIONS

Useful formulations of pentathiepins of this invention can be prepared in conventional ways. They include dusts, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions can be used primarily as concentrates which are to be diluted prior to ultimate use. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the approximate proportions set forth in Table 2 with the active ingredient plus at least one surfactant or diluent being equal to 100 weight percent.

TABLE 2

| | Weight Percent | | |
|---|---|---|---|
| | Active Ingredient | Diluent(s) | Surfactant(s) |
| Wettable Powders | 20–90 | 0–74 | 1–10 |
| Oil Suspensions, Solutions Emulsions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| High Strength Compositions | 90–99 | 0–10 | 0–2 |

Lower or higher levels of active ingredient can be present, depending on the intended use and the physical properties of the compound. Higher ratios of surfactant to active ingredient are sometimes desirable and are achieved by incorporation into the formulation, or by tank mixing.

Some typical solid diluents are described in Watkins et al., "Handbook of Insecticide Dust Diluents and Carriers", 2nd Ed., Dorland Books, Caldwell, N.J. but other solids, either mined or manufactured, can be used. The more absorptive diluents are preferred for wettable powders and the denser ones for dusts. Typical liquid diluents and solvents are described in Marsden, "Solvents Guide", 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia or Surface Active Agents", Chemical Publishing Co., Inc., N.Y., 1964, list surfactants and recommended uses. All formulations can contain minor amounts of additives to reduce foaming, caking, corrosion, microbiological growth, and the like.

Agricultural formulations that contain the compounds of this invention as active ingredient can also contain other active ingredients. The additional agricultural chemicals are employed in mixtures or combinations in amounts ranging from 0.05 to 25 parts by weight for each part by weight of the compound or compounds of this invention. The proper choice of amounts is readily made by one skilled in the art of protecting plants from pests. The following are illustrative of the agricultural chemicals that can be included in compositions or added to sprays containing one or more of the active compounds of this invention:

Fungicides:
methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyiminoacetamide (cymoxanil)
N-trichloromethylthiotetrahydrophthalimide (captan)
N-trichloromethylthiophthalimide (folpet)
dimethyl 4,4′-(o-phenylene)bis(3-thioallophanate) (thiophanate-methyl)
2-(thiazol-4-yl)benzimidazole (thiabendazole)
aluminum tris(O-ethyl phosphonate) (Aliette ®)
tetrachloroisophthalonitrile (chlorothalonil)
2,6-dichloro-4-nitroaniline (dichloran)
N-(2,6-dimethylphenyl)-N-(methoxyacetyl)alanine methyl ester (metalaxyl)
cis-N-[(1,1,2,2-tetrachloroethyl)thio]cyclohex-4-ene-1,2-dicarbioximide (captafol)
3-(3,5-dichlorophenyl)-N-(1-methylethyl)-2,4-dioxo-1-imidazolidine carboxamide (iprodione)
3-(3,5-dichlorophenyl)-5-ethenyl-5-methyl-2,4-oxazolidinedione (vinclozolin)
kasugamycin
O-ethyl-S,S-diphenylphosphorodithioate (edifenphos)
Bactericides:
tribasic copper sulfate
streptomycin sulfate
oxytetracycline
Acaricides:
senecioic acid, ester with 2-sec-butyl-4,6-dinitrophenol (binapacryl)

6-methyl-1,3-dithiolo [2,3-B]quinonolin-2-one (oxythioquinox)
2,2,2-trichloro-1,1-bis(4-chlorophenyl)ethanol (dicofol)
bis(pentachloro-2,4-cyclopentadien-1-yl) (dienochlor)
tricyclohexyltin hydroxide (cyhexatin)
hexakis(2-methyl-2-phenylpropyl)distannoxane (fenbutin oxide)

Nematicides:
2-[diethoxyphosphinylimino]-1,3-diethietane (fosthietan)
S-methyl-1-(dimethylcarbamoyl)-N-(methylcarbamoyloxy)thioformimidate (oxamoyl)
S-methyl-1-carbamoyl-N-(methylcarbamoyloxy)thioformimidate
N-isopropylphosphoramidic acid, O-ethyl-O'-[4-(methylthio)-m-tolyl]diester (fenamiphos)

Insecticides:
3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O,-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl N-[[(methylamino)carbonyl]oxy]ethanimidothioate (methomyl)
N'-(4-chloro-o-tolyl)-N,N-dimethylformamidine (chloridimeform)
O,O-diethyl-O-(2-isopropyl-4-methyl-6-pyrimidyl)-phosphorothioate (diazinon)
octachlorocamphene (toxaphene)
O-ethyl O-p-nitrophenyl phenylphosphonothioate (EPN)
cyano(3-phenoxyphenyl)-methyl 4-chloro-α-(1-methylethyl)benzeneacetate (fenvalerate)
(3-phenoxyphenyl)methyl (+)-cis,trans-3-(2,2-dichloroethenyl)-2,2-dimethylcyclopropanecarboxylate (permethrin)
dimethyl N,N'-[thiobis](N-methylimino)carbonyloxy]]-bis[ethanimidothioate](thiodicarb)
phosphorothiolothionic acid, O-ethyl-O-[4-(methylthio)phenyl]-S-n-propyl ester (sulprofos)
α-cyano-3-phenoxybenzyl[3-(2,2-dichlorovinyl)-2,2-dimethylcyclopropane]carboxylate (cypermethrin)
cyano(3-phenoxyphenyl)methyl 4-(difluoromethoxy-α-(methylethyl)benzeneacetate (Payoff®)
O,O-diethyl-O-(3,5,6-trichloro-2-pyridyl)phoshorothioate (chlorpyrifos)
O,O-dimethyl-S-[(4-oxo-1,2,3-benzotriazin-3-(4H)yl)-methyl]phosphorodithioate (azinphos-methyl)
5,6-dimethyl-2-dimethylamino-4-pyrimidinyl dimethyl carbamate (Pirimor®)
S-(N-formyl-N-methylcarbamoylmethyl)-O,O-dimethyl phosphorodithioate (formothion)
S-2-(ethylthioethyl)-O,O-dimethyl phosphiorothioate (demeton-S-methyl)
α-cyano-3-phenoxybenzyl cis-3-(2,2-dibromovinyl)-2,2-dimethylcyclopropane carboxylate (deltamethrin)
cyano(3-phenoxyphenyl)methyl ester of N-(2-chloro-4-trifluoromethylphenyl)alanine (Mavrik®).

The methods for making such compositions are well known. Solutions are prepared by simply mixing the ingredients. Fine solid compositions are made by blending and, usually, grinding as in a hammer or fluid energy mill. Suspensions are prepared by wet milling. Granules and pellets can be made by spraying the active material on preformed granular carriers or by agglomeration techniques.

Disease control is accomplished by applying the compounds of this invention to the portion of the plant to be protected. The compounds can be applied as preventive treatments prior to inoculation with the pathogen, or after inoculation as a curative post-infection treatment.

Rates of application for compounds of this invention will be influenced by specific host plants, fungal pathogens, and many factors of the environment must be determined under use conditions. Foliage sprayed with concentrations ranging from 1 to 500 ppm of active ingredient can be protected from disease under suitable conditions.

The pentathiepins of this invention are also useful as sulfur sensitizers that give low fog levels in light-sensitive colloid-silver halide emulsion layers. They are effective in both negative and positive emulsions. The compounds D, E and F are intermediates to G and hence have ultimate ultility in these photographic applications.

The silver halide emulsion can be any of the usual types employed for medical or industrial x-ray, graphic arts or portrait use. The silver halide crystal can also be any one of the usual types such as silver chloride, silver bromide, silver bromochloride or silver iodobromide. Particularly useful results have been obtained with high speed medical x-ray films containing silver iodobromide crystals. Gelatin is the preferred binder for the silver halide crystals but it can be partially or completely replaced with other natural or synthetic binders as known in the art. Thus, binders used to improve covering power, e.g., dextran, dextrin, polyvinyl pyrrolidone, as well as latices of polymers such as polyethyl acrylate which are useful in improving dimensional stability are advantageously included in many types of silver halide emulsions employed according to this invention.

The range of compound concentration depends on the emulsion used and on the particular compound employed. A useful range of concentration is from 0.002 to 0.5 mmole per mole of silver halide with a preferred range being about 0.01 to 0.1 mmole.

The support for the photographic element can be a polyethylene terephthalate film base as described in U.S. Pat. No. 2,627,088, but other coated and uncoated supports including those listed in U.S. Pat. No. 3,252,801 can also be used. Any of the usual emulsion adjuvants can be present in the silver halide layer, e.g., emulsion sensitizers, sensitizing dyes, coating aids, and the like.

One manner in which pentathiepins of this invention can be employed as sulfur sensitizers is as follows. They can be added in a digestion step to an aqueous gelatin dispersion of silver iodobromide. Gold thiocyanate can also be employed. The sulfur-sensitized photoemulsion formulation can then be coated on a support by one of ordinary skill in the art and worked up into film capable of a variety of specific end uses. One typical method for further workup is provided, for example, in U.S. Pat. No. 3,443,950.

The following Examples illustrate this invention. Kugelrohr refers to a bulb-to-bulb microdistillation assembly.

EXAMPLE 1

8-Bromo-7-methylpyrazolopentathiepin

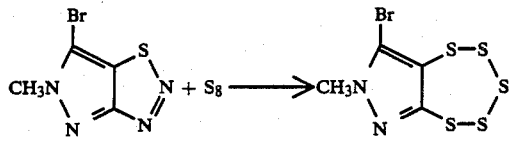

A mixture of sulfur (0.58 g, 2.28 mmol), 6-bromo-5-methylpyrazolo-1,2,3-thiadiazole (0.5 g, 2.28 mmol) and decahydronaphthalene was heated to 130° C. for 1.5 h while nitrogen was steadily evolved. The mixture was cooled and the decahydronaphthalene was removed by kugelrohr distillation. The residue was chromatographed on Silica Woelm®TSC (150 g, ether-hexane gradient) to give first sulfur and then 0.32 g, 44%, of 8-bromo-7-methylpyrazolopentathiepin as a sticky solid. A sample recrystallized from ether-hexane had mp 139° to 141° C. A sample prepared by a similar procedure had $^1$H-NMR (CDCl$_3$) σ 3.89 (s, 3H); IR (KBr) 1451, 1332 cm$^{-1}$.

Anal. Calcd for C$_4$H$_3$BrNS$_5$: C, 15.05; H, 0.95; S, 50.21. Found: C, 14.81; H, 1.06; S, 50.37.

EXAMPLE 2

8-Carboethoxy-7-methylpyrazolopentathiepin

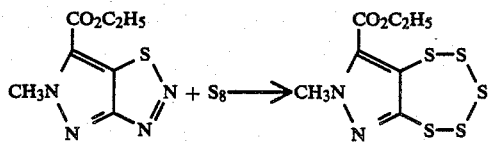

A mixture of sulfur (0.51 g, 2.03 mmol), 6-carboethoxy-5-methylpyrazolo-1,2,3-thiadiazole (0.43 g, 2.03 mmol) and decahydronaphthalene (5 mL) was heated to 170° to 175° C. for 1 h. The mixture was cooled and the decahydronaphthalene was removed by kugelrohr distillation. The residue was chromatographed on Silica Woelm®TSC (100 g, ether-hexane gradient) to give first sulfur then 0.24 g, 38%, of 8-carboethoxy-7-methylpyrazolopentathiepin as an oil, IR (neat) 1720, 1251, 1110 cm$^{-1}$; Mass spec. m/e 311.9198, m/e calcd for C$_7$H$_8$N$_2$O$_2$S$_5$ 311.9189. A sample kugelrohr distilled 150° C. (0.1 mm) had $^1$H-NMR (CDCl$_3$) σ 4.45 (q, 2H), 4.15 (s, 3H), 1.41 (t, 3H).

EXAMPLE 3

8-Cyano-7-methylpyrazolopentathiepin

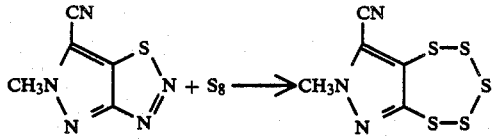

A mixture of sulfur (0.31 g, 1.21 mmol), 6-cyano-5-methylpyrazolo-1,2,3-thiadiazole (0.2 g, 1.21 mmol) and decahydronaphthalene (4 mL) was heated to 135° C. for 20 min while nitrogen gas was evolved. The mixture was cooled and the solvent was removed by kugelrohr distillation. The residue was chromatographed on Silica Woelm®TSC (100 g, ether-hexane gradient) to give first sulfur and then a mixture of product and impurities. This product fraction was purified by high pressure liquid chromatography (Zorbax®Sil, 50% methylene chloride) to give 0.04 g, 12%, of 8-cyano-7-methylpyrazolopentathiepin as an off-white solid, mp 112° to 124° C.; $^1$H-NMR (CDCl$_3$) σ 4.07 (s, 3H); IR (KBr) 2230 cm$^{-1}$; Mass spec. m/e 264.8943, m/e calcd for C$_5$H$_3$N$_3$S$_5$ 264.8930. A sample prepared in a similar experiment and recrystallized from ether-hexane had mp of 107° to 109° C.

EXAMPLE 4

6-Phenylthienopentathiepin

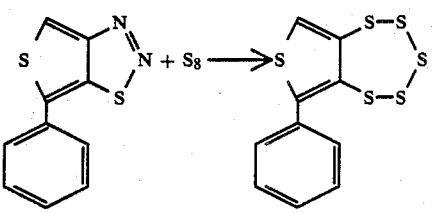

A mixture of sulfur (0.59 g, 2.29 mmol), 6-phenylthieno-1,2,3-thiadiazole (0.5 g, 2.29 mmol) and decalin (5 mL) was heated to 185° C. for 1 h while nitrogen gas was evolved. The mixture was cooled and the solvent was removed by kugelrohr distillation. The residue was dissolved in carbon disulfide and concentrated onto Silica Woelm®TSC and chromatographed on the same silica (150 g, 1% ether-hexane) to give first sulfur then 0.49 g, 67%, of 6-phenylthienopentathiepin as a yellow oil; $^1$H-NMR (CDCl$_3$) σ 7.68 (s, 1H), 7.45 (s, 5H); IR (neat) 743, 693 cm$^{-1}$; Mass spec. m/e 317.8765, m/e calcd for C$_{10}$H$_6$S$_6$ 317.8794.

EXAMPLE 5

5-Methylpyrazolo-1,2,3-thiadiazole

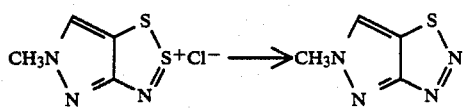

The compound, 5-methylpyrazolothiazathiolium chloride (30 g, 0.155 mol) was added all at once to a solution of 5% potassium hydroxide (500 mL) and sodium hydrosulfite (30 g, 0.172 mol). The resulting mixture was heated to 90° C. for 1 h; then it was cooled. Sodium nitrite (15 g, 0.217 mol) was dissolved in the clear light brown solution and it was added dropwise to 5% aqueous H$_2$SO$_4$ (600 mL) over 1.5 h. The mixture was stirred 20 min more; then it was brought to pH 9 with 20% aqueous NaOH and stirred overnight. The precipitate was filtered, rinsed with water, and air dried to give 7.45 g of product, mp 110° to 119° C. The filtrate was extracted with methylene chloride. Concentration of this extract gave another 4.54 g of product. The combined product was sublimed at 80° C. (0.3 mm) to give 8.14 g (37.5%) of 5-methylpyrazolo-1,2,3-thiadiazole as a colorless solid. A sample prepared by a similar procedure but recrystallized from methylene chloride-hexane had mp 125° to 127° C., $^1$H-NMR (CDCl$_3$) σ 7.7 (s, 1H), 4.25 (s, 3H); IR (KBr) 1289 cm$^{-1}$.

Anal. calcd for C$_4$H$_4$N$_4$S: C, 34.28; H, 2.88; N, 39.97. Found: C, 34.24; H, 2.98; N, 40.15.

EXAMPLE 6

6-Bromo-5-methylpyrazolo-1,2,3-thiadiazole

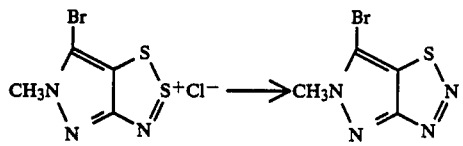

A solution of sodium hydrosulfite (3.4 g) in 5% aqueous potassium hydroxide (100 mL) was added to 6-bromo-5-methylpyrazolothiazathiolium chloride (3.55 g, 13.0 mmol) in an open beaker. The mixture was heated to 90° C. for 40 min, cooled and gravity filtered. Sodium nitrite (1.4 g) was dissolved in the clear yellow solution which was then added dropwise to 5% aqueous $H_2SO_4$ (300 mL) over 15 min. The mixture was stirred 2 h at ambient temperature then brought to pH 8–9 by addition of 20% aqueous sodium hydroxide. The reaction was extracted with methylene chloride. The organic layer was washed with brine and then filtered through a cone of sodium sulfate. Concentration gave 1.42 g of crude product which was sublimed at 65° C. (0.5 mm) to give 1.27 g, 44%, of 6-bromo-5-methylpyrazolo-1,2,3-thiadiazole. A sample prepared by a similar procedure had mp 99° to 101° C.; $^1$H-NMR (CDCl$_3$) $\sigma$ 4.2 (s, 3H); IR (KBr) 1308, 1275, 669 cm$^{-1}$; Mass spec. m/e 217.9263, m/e calcd for $C_4H_3BrN_4S$ 217.9262.

EXAMPLE 7

6-Carboethoxy-5-methylpyrazolo-1,2,3-thiadiazole

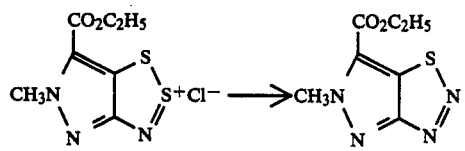

The compound, 6-carboethoxy-5-methylpyrazolothiazathiolium chloride (1.0 g, 3.77 mmol) was added to a solution of sodium hydrosulfite (1.2 g) in 5% aqueous sodium bicarbonate (25 mL) under a nitrogen atmosphere. The mixture was heated to 95° C. for 25 min; then it was cooled and gravity filtered. Bright yellow 5-carboethoxy-4-mercapto-3-amino-1-methylpyrazole disulfide (mp 149° to 150.5° C.) was removed by filtration. This, the major product if the reaction is run in air, can also be converted to the desired product by diazotization.

Sodium nitrite (0.6 g) was dissolved in the filtrate which was then added dropwise to 5% aqueous sulfuric acid (50 mL). The mixture was stirred 3 h followed by careful neutralization to pH 7 with solid sodium carbonate. The mixture was extracted with methylene chloride. The organic phase was washed with brine; then it was filtered through a cone of sodium sulfate and concentrated to leave 0.43 g, 53% of 6-carboethoxy-5-methylpryazolo-1,2,3-thiadiazole as an off-white solid, mp 91° to 94° C.; $^1$H-NMR (CDCl$_3$) $\sigma$ 4.55 (s, 3H), 4.45 (q, J=6.9 Hz, 2H), 1.4 (t, J=6.9 Hz, 3H). A sample recrystallized from ether-hexane had mp 94.5° to 96° C. A sample prepared by a similar procedure had:

Anal. calcd for $C_7H_8N_4O_2S$: C, 39.62; H, 3.80. Found: C, 39.99; H, 3.68, C, 40.09; H, 3.68.

EXAMPLE 8

6-Carbomethoxy-5-methylpyrazolo-1,2,3-thiadiazole

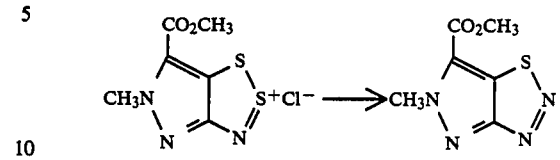

The compound, 6-carbomethoxy-5-methylpyrazolothiazathiolium chloride (4.22 g, 16.8 mmol) was added to a solution of sodium hydrosulfite (5.07 g) and 5% aqueous sodium bicarbonate (105 mL) in an open flask. The mixture was heated to 90° C. for 45 min, cooled, and gravity filtered. Sodium nitrite (2.53 g) was dissolved in the filtrate which was then added dropwise to 5% aqueous sulfuric acid (265 mL) over 30 min. The reaction was stirred 2 h at ambient temperature; then it was carefully neutralized with solid potassium carbonate and extracted with methylene chloride. The organic phase was washed with brine, filtered through a cone of sodium sulfate and concentrated. The residue was chromatographed on Silica Woelm®TSC (200 g, methylene chloride) to give 0.9 g, 27%, of 6-carbomethoxy-5-methylpyrazolo-1,2,3-thiadiazole as a white solid; mp 115° to 121° C.; $^1$H-NMR (CDCl$_3$) $\sigma$ 4.57 (s, 3H), 4.02 (s, 3H); IR (KBr) 1736, 1443, 1272 cm$^{-1}$; Mass spec. m/e 198.0204, m/e calcd for $C_6H_6N_4O_2S$ 198.0211.

EXAMPLE 9

5-Methylpyrazolo-1,2,3-thiadiazole-6-carboxylic Acid

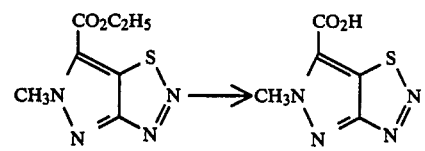

The compound, 6-carboethoxy-5-methylpyrazolo-1,2,3-thiadiazole (1.75 g, 8.25 mmol) was added to 5% aqueous sodium hydroxide (20 mL) and the mixture was warmed with stirring until dissolution occurred. The solution was filtered and acidified to pH 4 with conc HCl and filtered again. The solvent was removed under vacuum at 40° C. The solid was then dried under vacuum overnight to leave 2.48 g of a crude mixture of NaCl and 5-methylpyrazolo-1,2,3-thiadiazole-6-carboxylic acid. A sample prepared by the method of Example 7 in which sodium bicarbonate was replaced by sodium hydroxide and recrystallized from toluene had mp 192° to 194° C.; $^1$H-NMR (DMSO-d$_6$) $\sigma$ 4.3 (s, 3H); IR (KBr) 3430, 1718, 1442, 1280 cm$^{-1}$; Mass spec. m/e 184.0048; m/e calcd for $C_4H_4N_4O_2S$ 184.0055.

EXAMPLE 10

5-Methylpyrazolo-1,2,3-thiadiazole-6-carboxylic Acid Chloride

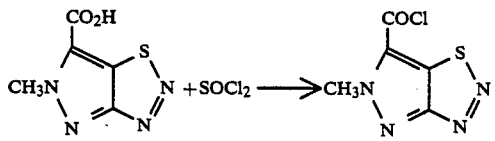

Thionyl chloride (20 mL) was added dropwise under nitrogen atmosphere to a stirred, crude mixture of 5-methylpyrazolo-1,2,3-thiadiazole-6-carboxylic acid and NaCl (2.48 g). The reaction was endothermic as gas gently evolved. The mixture was stirred 3 h at ambient temperature; then it was filtered under nitrogen. The filtrate was concentrated leaving 2.1 g of solid. The recovered 2.1 g of starting material was slurried in chloroform (30 mL) and thionyl chloride (20 mL) was added. This mixture was refluxed for 18 h and most of the solid was dissolved. The mixture was cooled and filtered under nitrogen. The solvent was removed from the filtrate under vacuum leaving 1.1 g of 5-methylpyrazolo-1,2,3-thiadiazole-6-carboxylic acid chloride as a waxy yellow solid, IR (CHCl$_3$ solution) 1758 cm$^{-1}$.

EXAMPLE 11

5-Methylpyrazolo-1,2,3-thiadiazole-6-carboxamide

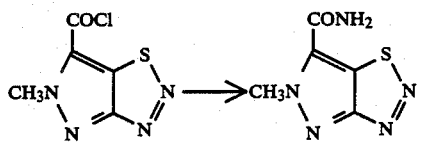

Ammonia (gas) was bubbled into a solution of 5-methyl-pyrazolo-1,2,3-thiadiazole-6-carboxylic acid chloride (1.1 g) and methylene chloride (30 mL) until no more solid formed. Ethyl acetate (60 mL) and water (30 mL) were added and the phases were separated. The aqueous phase was extracted with ethyl acetate (2×20 mL). The combined organic phase was washed with brine; then it was filtered through a cone of sodium sulfate and concentrated to leave 0.9 g of 5-methyl-pyrazolo-1,2,3-thiadiazole-6-carboxamide as a pink solid. A sample recrystallized from acetone-hexane had mp 183° to 184.5° C.; $^1$H-NMR (acetone-d$_6$) σ 7.3 (broad s, 2H), 4.5 (s, 3H); IR (KBr) 1695 cm$^{-1}$; Mass spec. m/e 183.0208; m/e calcd for C$_5$H$_5$N$_5$OS 183.0215.

EXAMPLE 12

6-Cyano-5-methylpyrazolo-1,2,3-thiadiazole

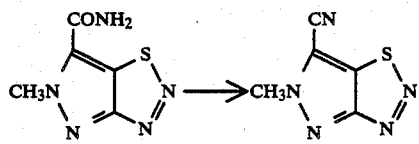

The compound, 5-methylpyrazolo-1,2,3-thiadiazole-6-carboxamide (0.9 g, 4.92 mmol) was slurried in toluene (10 mL) and thionyl chloride (0.5 mL) was added. The mixture was heated to 80° C. and then to 105° C. with no reaction. The mixture was cooled to 70° C. and ethyl acetate (10 mL) was added. The slurry was stirred at 70° to 80° C. for 55 h, cooled and concentrated onto Silica Woelm®TSC and chromatographed on 50 g of the same silica (25% ether-hexane) to give after a 300 mL forerun 0.2 g of 6-cyano-5-methylpyrazolo-1,2,3-thiadiazole as a light yellow solid; mp 111° to 114° C.; $^1$H-NMR (CDCl$_3$) σ 4.41 (s, 3H); IR (KBr) 2230, 1332, 679 cm$^{-1}$; Mass spec. m/e 165.0109; m/e calcd. for C$_5$H$_3$N$_5$S 165.0109.

Continued elution with ethyl acetate eluted 0.5 g of starting material. This solid was dissolved in ethyl acetate (50 mL) and thionyl chloride (3 mL) was added. This solution was refluxed under nitrogen 4 days, cooled, concentrated onto silica and chromatographed on 50 g of silica (25% ether-hexane) to give 0.29 g more product. In this manner, 0.49 g (60%) of 6-cyano-5-methylpyrazolo-1,2,3-thiadiazole was prepared.

EXAMPLE 13

5-Methylpyrazolothiazathiolium Chloride

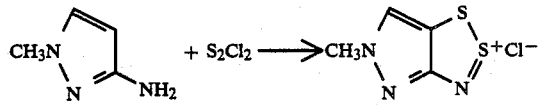

Sulfur monochloride (100 mL) was cooled to 0° C. and 3-amino-1-methylpyrazole (17.48 g, 180 mmol) in acetic acid (28 mL) was added dropwise over 10 min. The resulting mixture was warmed to ambient temperature; then it was gradually heated to 65° C. over 3 h and maintained at 65° C. for 2 h. The mixture was cooled and benzene (240 mL) was added. The precipitate was filtered and rinsed with benzene to give 32.5 g, 93%, of 5-methylpyrazolothiazathiolium chloride as a bright orange solid; IR (KBr) 1646, 1116, 712 cm$^{-1}$; UV (trifluoroacetic acid) 452 nm (ε=1590), 326 nm (ε=10200); a sample prepared by a similar procedure decomposed above 190° C.

EXAMPLE 14

6-Bromo-5-methylpyrazolothiazathiolium Chloride

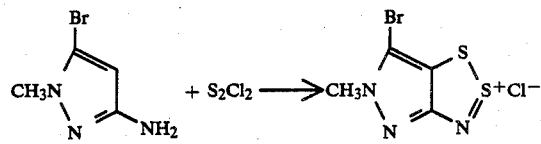

Sulfur monochloride (16 mL) was chilled to 0° C. under a nitrogen atmosphere and 5-bromo-3-amino-1-methylpyrazole (3.52 g, 20 mmol) in acetic acid (8 mL) was added dropwise over 10 min. The resulting mixture was warmed to 65° C. over 2 h and stirred at 65° C. for 2 h more. The reaction was diluted with benzene (80 mL), cooled to ambient temperature and filtered under nitrogen. The solid was rinsed with benzene until the washing remained colorless and dried with a stream of nitrogen to give 4.05 g, 74%, of 6-bromo-5-methyl-pyrazolothiazathiolium chloride as a free flowing pink solid which decomposed at 200° C. A sample prepared by a similar procedure but not filtered and dried under nitrogen had UV (trifluoroacetic acid) 500 nm (ε=1180), 328 nm (ε=8660).

EXAMPLE 15

6-Carboethoxy-5-methylpyrazolothiazathiolium Chloride

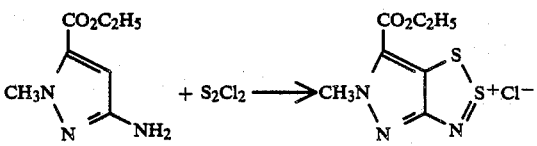

Sulfur monochloride (3.3 mL) was chilled to 0° C. and 5-carboethoxy-3-amino-1-methylpyrazole (1.0 g, 5.9 mmol) in acetic acid (1.3 mL) was added dropwise over 5 min. The mixture was warmed to 40° C. and stirred at this temperature for 4 h. The mixture was cooled and diluted with benzene (20 mL); then it was filtered under nitrogen and rinsed with 3 portions of benzene. The yellow solid was dried under a stream of nitrogen to give 0.7 g, 45%, of 6-carboethoxy-5-methyl-pyrazolothiazathiolium chloride as a bright yellow solid; mp 98° (decomp.); UV (trifluoroacetic acid) 442 nm ($\epsilon$=1470), 328 nm ($\epsilon$=8100).

EXAMPLE 16

6-Carbomethoxy-5-methylpyrazolothiazathiolium Chloride

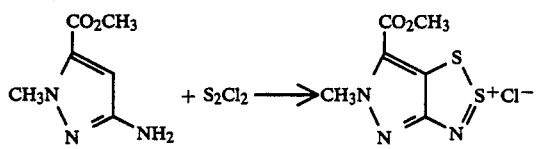

Sulfur monochloride (13 mL) was chilled to 0° C. under a nitrogen atmosphere and 5-carbomethoxy-3-amino-1-methylpyrazole (4.0 g, 25.8 mmol) dissolved in warm acetic acid (5 mL) was added dropwise over 10 min. The mixture was gradually warmed to 40° C. and stirred at this temperature 2 h. The reaction was cooled and benzene (50 mL) was added. The solid was filtered under nitrogen, rinsed with benzene and dried under a stream of nitrogen to give 4.22 g, 65%, of 6-carbomethoxy-5-methyl-pyrazolothiazathiolium chloride as a bright yellow solid.

EXAMPLE 17

5-Carboethoxy-3-(2,5-dimethylpyrrolyl)-1-methyl-pyrazole

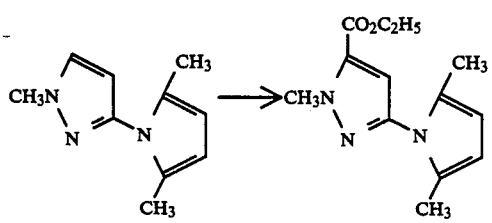

A solution of 3-(2,5-dimethylpyrrolyl)-1-methyl-pyrazole (5.0 g, 28.6 mmol) in dry tetrahydrofuran (250 mL) was cooled to −78° C. Then, n-butyllithium (19.5 mL, 1.6M, 31.2 mmol) was added dropwise over 15 min followed by stirring for 2 h at −78° to −60° C. Ethyl chloroformate (3.58 mL, 37.5 mmol) was added and the solution was warmed to room temperature and stirred 1 h. The solvent was removed at reduced pressure and the residue was partitioned between ether and water. Phases were separated and the organic layer was washed with brine, filtered through a cone of sodium sulfate, and concentrated to leave an oil. This residue was chromatographed on Silica Woelm®TSC (600 g, 15% ether-hexane) to give after an 850 mL forerun, 0.18 of an impurity in 500 mL and 4.69 g of oil in 700 mL. The oil was kugelrohr distilled, 100° to 110° C., (0.15 mm) to give 4.24 g, 60% of 5-carboethoxy-3-(2,5-dimethylpyrrolyl)-1-methylpyrazole as a clear oil; IR (neat) 1728, 1546, 1494, 1273, 1252 cm$^{-1}$.

Anal. calcd for $C_{13}H_{17}N_3O_2$: C, 63.14; H, 6.93; N, 16.99. Found: C, 62.83; H, 6.93; N, 16.67.

A sample prepared by a similar procedure had:

$^1$H-NMR (CDCl$_3$) $\sigma$ 6.78 (s, 1H), 5.9 (s, 2H), 4.38 (q, 2H), 4.21 (s, 3H), 2.1 (s, 6H), 1.4 (t, 3H).

EXAMPLE 18

5-Bromo-3-(2,5-dimethylpyrrolyl)-1-methylpyrazole

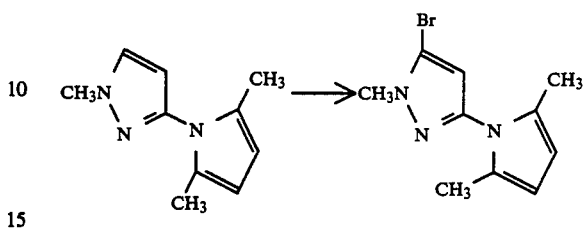

A solution of 3-(2,5-dimethylpyrrolyl)-1-methyl-pyrazole (2.0 g, 11.4 mmol) and dry tetrahydrofuran (100 mL) was cooled to −78° C. and n-butyllithium (7.8 mL, 1.6M, 12.48 mmol) was added over 3 min. The solution was stirred 1.5 h at −78° C., then a solution of cyanogen bromide (1.3 g, 12.5 mmol) in tetrahydrofuran (3 mL) over a spatula of sodium sulfate (to dry the BrCN) was taken from the drying agent and syringed into the reaction. The mixture was warmed to ambient temperature and stirred overnight. The solvent was removed at reduced pressure and the residue was partitioned between ether and water. The phases were separated and the organic layer was washed with brine, filtered through a cone of sodium sulfate and concentrated. The residue was chromatographed on Silica Woelm TSC (200 g, 25% ether-hexane) to give 2.22 g, 76%, of 5-bromo-3-(2,5-dimethylpyrrolyl)-1-methyl-pyrazole as a white solid, mp 66° to 69° C. A sample prepared by a similar procedure had IR (KBr) 1528 cm$^{-1}$; $^1$H-NMR (CDCl$_3$) $\sigma$ 6.2 (s, 1H), 5.83 (s, 2H), 3.88 (s, 3H), 2.1 (s, 6H). An analytical sample was sublimed 55° C. (0.3 mm).

Anal. calcd for $C_{10}H_{12}BrN_3$: C, 47.26; H, 4.76; N, 16.53. Found: C, 46.96; H, 4.66; N, 16.28.

EXAMPLE 19

5-Chloro-3-(2,5-dimethylpyrrolyl)-1-methylpyrazole

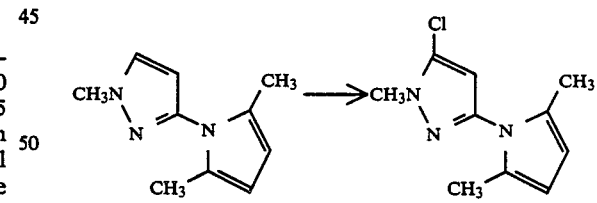

A solution of 3-(2,5-dimethylpyrrolyl)-1-methyl-pyrazole (0.2 g, 1.14 mmol) in tetrahydrofuran (10 mL) was cooled to −78° C. and n-butyllithium (0.78 mL, 1.6M, 1.25 mmol) was added over 3 min. The mixture was stirred 1.5 h at −78° C.; then cyanogen chloride (0.5 mL) was bubbled in. The mixture was allowed to warm to ambient temperature and stirred 1 h. The solvent was removed at reduced pressure and the residue was partitioned between ether and water. The phases were separated and the organic layer was washed with brine, filtered through a cone of sodium sulfate, and concentrated. The residue was purified by preparative thin layer chromatography (25% ether-hexane) to give 0.1 g of 5-chloro-3-(2,5-dimethylpyrrolyl)-1-methyl-pyrazole as an oil which solidified to a colorless solid;

Rf=0.3; mp 59° to 61° C.; ¹H-NMR (CDCl₃) σ 6.1 (s, 1H), 5.84 (s, 2H), 3.84 (s, 3H), 2.1 (s, 6H); IR (KBr) 1529 cm⁻¹. A sample sublimed 50° C. (0.3 mm) had mp 60° to 63° C.:

Anal. calcd for C₁₀H₁₂ClN₃: C, 57.28; H, 5.77; N, 20.04. Found: C, 57.00; H, 5.82; N, 19.81.

EXAMPLE 20

5-Carbomethoxy-3-(2,5-dimethylpyrrolyl)-1-methylpyrazole

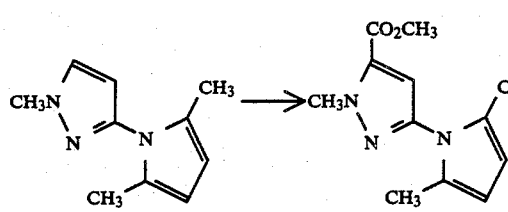

A solution of 3-(2,5-dimethylpyrrolyl)-1-methylpyrazole (10.0 g, 57.1 mmol) in tetrahydrofuran (300 mL) was cooled to −78° C. and n-butyllithium (39.3 mL, 1.6M, 62.88 mmol) was added over 10 min. The mixture was stirred 1.5 h at −78° C.; then, methyl chloroformate (8.8 mL, 114 mmol) was added all at once. The mixture was warmed to ambient temperature and stirred for 1 h. The solvent was removed at reduced pressure and the residue was partitioned between ether and water. The phases were separated and the organic layer was washed with brine, filtered through a cone of sodium sulfate and concentrated. The residue was chromatographed on Silica Woelm TSC (600 g, 15% ether-hexane) to give 8.52 g, 64%, of 5-carbomethoxy-3-(2,5-dimethylpyrrolyl)-1-methylpyrazole as a white solid; mp 63° to 65° C.; ¹H-NMR (CDCl₃) σ 6.7 (s, 1H), 5.8 (s, 2H), 4.2 (s, 3H), 3.85 (s, 3H), 2.1 (s, 6H).

EXAMPLE 21

5-Carboethoxy-3-amino-1-methylpyrazole

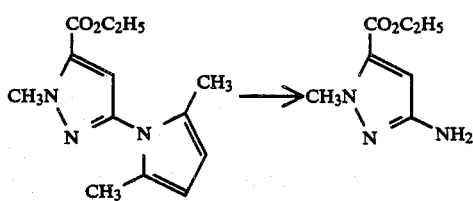

A solution of potassium hydroxide (0.20 g, 3.58 mmol) in water (3 mL) and ethanol (3 mL) was added to a slurry of hydroxylamine hydrochloride (0.47 g, 7.15 mmol) in ethanol (5 mL). Then, 5-carboethoxy-3-(2,5-dimethylpyrrolyl)-1methylpyrazole (0.35 g, 1.43 mmol) was added and the mixture was refluxed 48 h, cooled, and neutralized to pH 7-8 with ammonium hydroxide. The solvents were removed at reduced pressure and the residue was triturated with ether. Calcium sulfate was added and the heterogeneous mixture was filtered. The solvent was removed at reduced pressure and the residue was chromatographed on Silica Woelm ®TSC (25 g, 2:1 hexane-ethyl acetate) to give 0.17 g, 70%, of 5-carboethoxy-3-amino-1-methylpyrazole as an off-white solid, mp 57° to 58° C.; IR (KBr) 3420, 1720, 1550, 1488, 1268, 1102 cm⁻¹; ¹H-NMR (CDCl₃) σ 6.14 (s, 1H), 4.31 (q, 2H), 3.97 (s, 3H), 3.4 (br s, 2H), 1.33 (t, 3H).

A sample sublimed at 35° C. (0.15 mm) had mp 58° to 60° C.:

Anal. calcd for C₇H₁₁N₃O₂: C, 49.70; H, 6.55; N, 24.84. Found: C, 49.72; H, 6.43; N, 24.57.

EXAMPLE 22

5-Bromo-3-amino-1-methylpyrazole

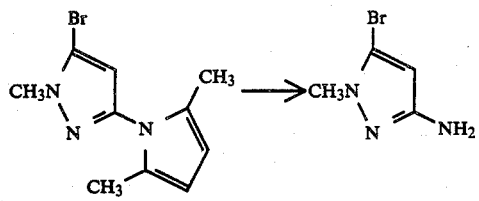

A solution of potassium hydroxide (0.4 g, 7.15 mmol) in water (6 mL) and ethanol (6 mL) was added to a slurry of hydroxylamine hydrochloride (0.94 g, 14.3 mmol) in ethanol (10 mL). Then 5-bromo-3-(2,5-dimethylpyrrolyl)-1-methylpyrazole (0.72 g, 2.84 mmol) was added and the mixture was refluxed 60 h. The solvents were removed at reduced pressure and the residue was triturated with ether. Sodium sulfate was added and the heterogeneous mixture was filtered. The solvent was evaporated from the filtrate and the residue was chromatographed on Silica Woelm®TSC (100 g, ethyl acetate-hexane gradient) to give 0.43 g, 86%, of 5-bromo-3-amino-1-methylpyrazole as an off-white solid; mp 53° to 55° C.; ¹H-NMR (CDCl₃) σ 5.63 (s, 1H), 3.68 (s, 3H), 3.9-3.4 (br s, 2H); IR (KBr) 3388, 3310, 1548, 1484, 750 cm⁻¹. A sample sublimed at 30° C. (0.18 mm) had mp 54° to 56° C.:

Anal. calcd for C₄H₆BrN₃: C, 27.30; H, 3.44; N, 23.87. Found: C, 27.27; H, 3.43; N, 23.59.

EXAMPLE 23

5-Carbomethoxy-3-amino-1-methylpyrazole

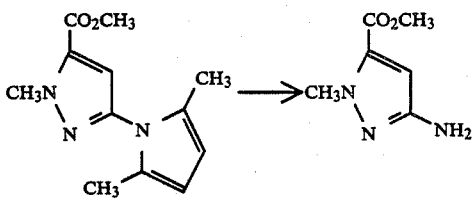

A solution of potassium hydroxide (5.08 g, 90.7 mmol) in water (76 mL) and ethanol (76 mL) was added to a slurry of hydroxylamine hydrochloride (11.44 g, 169.5 mmol) in ethanol (127 mL). Then, 5-carbomethoxy-3-(2,5-dimethylpyrrolyl)-1-methylpyrazole (8.5 g, 36.6 mmol) was added and the mixture was refluxed under a nitrogen atmosphere for 65 h. The solvents were removed at reduced pressure and the residue was triturated with ether. Sodium sulfate was added and the heterogenous mixture was filtered. The filtrate was concentrated and the residue was chromatographed on Silica Woelm®TSC (300 g, ethyl acetate-hexane gradient) to give 4.61 g, 81% of 5-carbomethoxy-3-amino-1-methylpyrazole as a white solid mp 114° to 118° C.; ¹H-NMR (CDCl₃) σ 6.17 (s, 1H), 4.02 (s, 3H), 3.88 (s, 1H), 3.7 (br s, 2H); IR (KBr) 1719, 1551, 1263, 1102, 756 cm⁻¹.

EXAMPLE 24

5-Chloro-3-amino-1-methylpyrazole

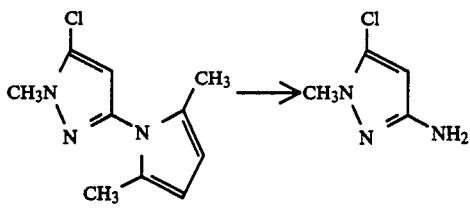

The above-named compound can be made from 5-chloro-3-(2,5-dimethylpyrrolyl)-1-methylpyrazole by the general procedure of Example 22.

The embodiments of the invention in which an exclusive property or privilege is claimed are defined as follows:

1. Hetero-ring fused pentathiepins of the formula:

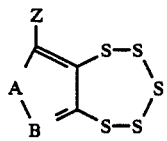

A is $R^1N$,
B is N,
Z is halogen, CN, $OR^4$, $SR^4$, $NR^5R^4$, $COOR^4$, $COSR^4$, or $CONR^5R^4$, and
$R^1$, $R^4$, and $R^5$ are the same or different and are selected from the group H, except that $R^1$ is not H, $C_1$ to $C_6$ straight or branched alkyl, $C_3$ to $C_6$ cycloalkyl, phenyl, naphthyl and substituted phenyl and naphthyl with 1 to 5 hydrogen atoms of phenyl and 1 to 7 hydrogen atoms of naphthyl substituted with substituents selected from the group $R^6$, halogen, $OR^6$, $NR_2^6$ with $R^6 = C_1$ to $C_6$ straight or branched alkyl.

2. Hetero-ring fused pentathiepins according to claim 1 wherein:
Z is halogen, CN, and $COOR^4$,
$R^1$, and $R^4$ are the same or different and are selected from the group H, except that $R^1$ is not H, $C_1$ to $C_6$ straight or branched alkyl, $C_3$ to $C_6$ cycloalkyl, phenyl, naphthyl and substituted phenyl and naphthyl with 1 to 5 hydrogen atoms of phenyl and 1 to 7 hydrogen atoms of naphthyl substituted with substituents selected from the group $R^6$, halogen, $OR^6$, $NR_2^6$ with $R^6 = C_1$ to $C_6$ straight or branched alkyl.

3. Hetero-ring fused pentathiepins according to claim 2 wherein:
Z is halogen or CN, and
$R^1$ and $R^4$ are the same or different and are selected from the group $C_1$ to $C_6$ straight or branched alkyl, $C_3$ to $C_6$ cycloalkyl, phenyl, naphthyl and substituted phenyl and naphthyl with 1 to 5 hydrogen atoms of phenyl and 1 to 7 hydrogen atoms of naphthyl substituted with substituents selected from the group $R^6$, halogen, $OR^6$, $NR_2^6$ with $R^6 = C_1$ to $C_6$ straight or branched alkyl.

4. A compound according to claim 2, 8-carboethoxy-7-methylpyrazolopentathiepin.

5. A compound according to claim 3, 8-bromo-7-methylpyrazolopentathiepin.

6. A compound according to claim 3, 8-cyano-7-methylpyrazolopentathiepin.

* * * * *